(12) United States Patent
Shinobu

(10) Patent No.: US 10,620,199 B2
(45) Date of Patent: *Apr. 14, 2020

(54) SENSING SENSOR AND SENSING METHOD

(71) Applicant: NIHON DEMPA KOGYO CO., LTD., Tokyo (JP)

(72) Inventor: Wakako Shinobu, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 305 days.

This patent is subject to a terminal disclaimer.

(21) Appl. No.: 15/438,766

(22) Filed: Feb. 22, 2017

(65) Prior Publication Data

US 2017/0248591 A1 Aug. 31, 2017

(30) Foreign Application Priority Data

Feb. 29, 2016 (JP) .................................. 2016-037935

(51) Int. Cl.
*G01N 33/551* (2006.01)
*G01N 33/543* (2006.01)
*G01N 29/02* (2006.01)

(52) U.S. Cl.
CPC ..... *G01N 33/54373* (2013.01); *G01N 29/022* (2013.01); *G01N 2291/0255* (2013.01)

(58) Field of Classification Search
None
See application file for complete search history.

(56) References Cited

U.S. PATENT DOCUMENTS

| 5,658,732 A * | 8/1997 | Ebersole | ............... | C12Q 1/6825 |
| | | | | 422/68.1 |
| 9,625,420 B2 * | 4/2017 | Kukita | ................. | G01N 29/036 |
| 2009/0087925 A1* | 4/2009 | Wagner | ................... | B01F 5/061 |
| | | | | 436/518 |

(Continued)

FOREIGN PATENT DOCUMENTS

| JP | 2007040703 | 2/2007 |
| JP | 2007178305 | 7/2007 |

(Continued)

OTHER PUBLICATIONS

"Office Action of Japan Counterpart Application," with English translation thereof, dated Nov. 12, 2019, p. 1-p. 7.

*Primary Examiner* — Christopher L Chin
(74) *Attorney, Agent, or Firm* — JCIPRNET

(57) ABSTRACT

A sensing sensor includes a wiring board, a piezoelectric resonator, and a gel-like protective agent. The piezoelectric resonator has one surface side on which an adsorbing film is formed. The adsorbing film is constituted of biomolecules. The protective agent is disposed so as to cover a surface of the adsorbing film. The protective agent is configured to suppress an inactivation of the biomolecules. The channel forming member is disposed so as to cover a region of the one surface side of the wiring board including the piezoelectric resonator. The channel forming member includes an injection port of the sample solution. The flow passage is disposed between the wiring board and the channel forming member. The flow passage is configured to allow the sample solution supplied to the injection port to flow from one end side to another end side on the one surface side of the piezoelectric resonator.

4 Claims, 12 Drawing Sheets

(56) References Cited

U.S. PATENT DOCUMENTS

| | | |
|---|---|---|
| 2010/0200428 A1 | 8/2010 | Choi et al. |
| 2011/0124130 A1* | 5/2011 | Wagner ............ G01N 33/54366 436/518 |
| 2014/0250985 A1* | 9/2014 | Shinobu ............... G01N 29/022 73/64.53 |
| 2015/0090035 A1* | 4/2015 | Kukita ................. G01N 29/036 73/579 |
| 2017/0184577 A1* | 6/2017 | Kukita ............. G01N 33/48792 |

FOREIGN PATENT DOCUMENTS

| | | |
|---|---|---|
| JP | 2009175163 | 8/2009 |
| JP | 2010534831 | 11/2010 |
| JP | 2012145566 | 8/2012 |
| JP | 2012145566 A * | 8/2012 |
| JP | 2015068747 | 4/2015 |

* cited by examiner

SENSING SENSOR AND SENSING METHOD

CROSS-REFERENCE TO RELATED APPLICATIONS

This application is based on and claims priority under 35 U.S.C. § 119 to Japanese Patent Application No. 2016-037935, filed on Feb. 29, 2016, the entire content of which is incorporated herein by reference.

TECHNICAL FIELD

This disclosure relates to a sensing sensor and a sensing method for sensing a sensing object contained in a sample solution based on an oscillation frequency of a piezoelectric resonator.

DESCRIPTION OF THE RELATED ART

As a sensing method of a sensing object in a sample fluid, for example, a trace amount of protein in blood or serum, there is disclosed a sensing sensor, for example, using a Quartz Crystal Microbalance (QCM) as disclosed in Japanese Unexamined Patent Application Publication No. 2012-145566. The QCM uses a crystal resonator where an adsorbing film that is constituted of such as an antibody and adsorbs a sensing object as an antigen by antigen-antibody reaction is arranged on a surface of an excitation electrode. The QCM grasps a load by the mass of the adsorbed sensing object in a sample solution as a frequency variation of the crystal resonator, and thus the sensing object is quantitated. The use of the basic principle allows application to simple measurement employed for diagnosis in a medical front and food inspection.

In a sensing device, for a simplicity of a measuring method and an efficiency in measuring many sample solutions, a sensing sensor part that includes a crystal resonator, on which an adsorbing film is disposed, is configured to be removable to a device main body, so as to connect a new sensing sensor to the device main body in performing the measurement of the sensing object to perform the measurement. Then, since repeatedly injecting the sample solution to the identical sensing sensor decreases an adsorption power of the adsorbing film, the sensing sensor used for the measurement is removed and a new sensing sensor is connected to perform the measurement, thus maintaining a sensing accuracy.

Since a plurality of new sensing sensors are held and replaced to perform the measurement, the sensing sensor is sometimes stored in a new condition over a long period of time. However, for example, when the sensing sensor that includes the adsorbing film using biomolecules such as the antibody is stored over a long period of time, protein constituting the adsorbing film is sometimes denatured or decomposed to be inactivated due to such as drying, so as to decrease the adsorption capacity to decrease the measurement accuracy.

Japanese Unexamined Patent Application Publication No. 2007-40703 discloses a sensing sensor that forms a photoresist protective film on a surface of a metal electrode and subsequently irradiates the photoresist protective film with a light to harden, so as to reduce an adhesion of contaminants, such as dirt, to the metal electrode. However, there is no description on protection of an adsorbing layer that is disposed on the electrode and constituted of the biomolecules such as the antibody.

PRIOR ART DOCUMENT

Patent Document

[Patent Document 1] Japanese Unexamined Patent Application Publication No. 2012-145566.
[Patent Document 2] Japanese Unexamined Patent Application Publication No. 2007-40703.

A need thus exists for a sensing sensor and sensing method which are not susceptible to the drawback mentioned above.

SUMMARY

According to an aspect of this disclosure, there is provided a sensing sensor including a wiring board, a piezoelectric resonator, a protective agent, a channel forming member, and a flow passage. The wiring board is configured to include a connection terminal and a depressed portion. The connection terminal is for connection to a measuring device for measuring an oscillation frequency. The depressed portion is formed on one surface side of the wiring board. The piezoelectric resonator is configured to include a piezoelectric piece and an excitation electrode on the piezoelectric piece. The piezoelectric resonator is secured to the wiring board such that the piezoelectric resonator covers the depressed portion and a vibrating region is opposed to the depressed portion. The excitation electrode is electrically connected to the connection terminal. The piezoelectric resonator has one surface side on which an adsorbing film constituted of biomolecules for adsorbing a sensing object in a sample solution is formed. The gel-like protective agent has a high viscosity. The protective agent is disposed so as to cover a surface of the adsorbing film for suppressing an inactivation of the biomolecules. The channel forming member is disposed to cover a region of the one surface side of the wiring board including the piezoelectric resonator. The channel forming member includes an injection port of the sample solution. The flow passage is disposed between the wiring board and the channel forming member. The flow passage is configured to allow the sample solution supplied to the injection port to flow from one end side to another end side on the one surface side of the piezoelectric resonator.

According to another aspect of this disclosure, there is provided a sensing method for sensing a sensing object based on a vibration frequency of a piezoelectric resonator by oscillating the piezoelectric resonator having an adsorbing film constituted of biomolecules for adsorbing the sensing object contained in a sample solution. The sensing method includes a step of connecting the above-described sensing sensor to the measuring device, a step of injecting a remover for removing the protective agent into the injection port to allow the remover to flow through the flow passage so as to remove the protective agent by the remover, and a step of subsequently injecting the sample solution into the injection port to sense the sensing object.

According to this disclosure, the sensing sensor includes a crystal resonator that includes an adsorbing film constituted of the biomolecules for adsorbing the sensing object on the excitation electrode. The sensing sensor allows the sample solution to flow through one surface side of the crystal resonator, so as to adsorb the sensing object on the adsorbing film. In the sensing sensor, the protective agent of a high viscosity material is applied so as to cover the surface of the adsorbing film. Therefore, the deterioration of the biomolecules due to drying of the adsorbing film or the like can be suppressed, thus inhibiting the decrease of the measurement accuracy due to the storage. When using the sensing sensor, the protective agent can be removed by allowing the remover to flow through the flow passage disposed on the sensing sensor to allow the sample solution to flow on the front surface of the crystal resonator. Accordingly, a simple operation ensures the adsorbing film to be exposed so as to perform the measurement of the sensing object.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

The following describes a sensing device using a sensing sensor according to an embodiment of this disclosure. This sensing device uses a microfluidic chip. The sensing device is configured to detect, for example, presence/absence of an antigen, such as virus, in a sample solution obtained from nasal cavity swab of a human so as to determine whether the human has been infected with a virus or not with the microfluidic chip. As illustrated in an external perspective view in FIG. 1, the sensing device includes a main body 12 as a measuring device and a sensing sensor 2. The sensing sensor 2 is attachably/detachably connected to an insertion port 17 that is formed in the main body 12. The main body 12 includes, for example, a display 16 constituted by a liquid crystal display screen on a top surface. The display 16 displays, for example, an output frequency of an oscillator circuit, which is disposed in the main body 12 and will be described later, a measurement result of such as an amount of frequency variation, presence/absence of detected sensing object or a similar result.

Figure 1:
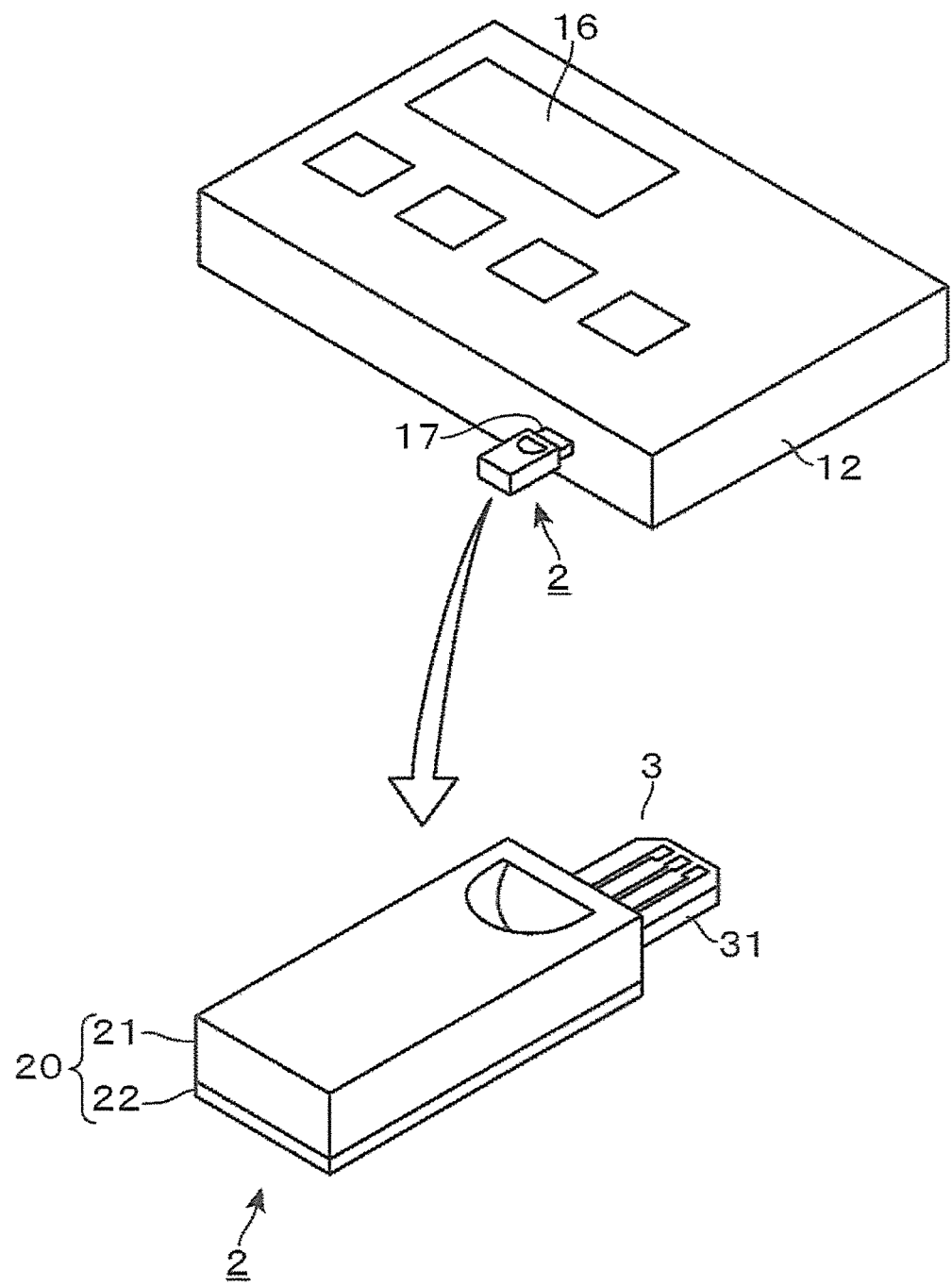
FIG. 1 is a perspective view of a sensing device and a sensing sensor according to this disclosure.
Figure 2:
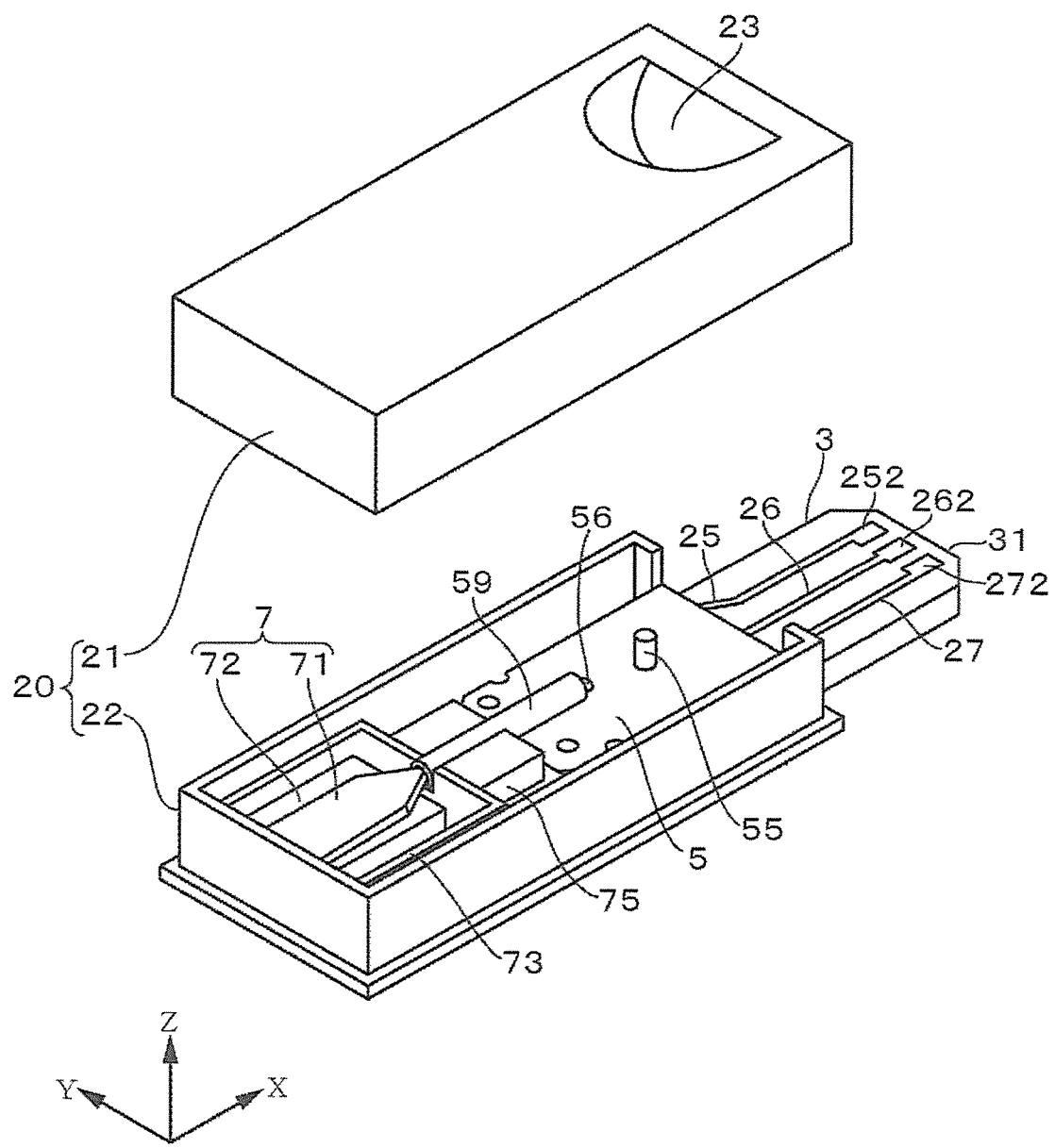
FIG. 2 is an exploded perspective view of the sensing sensor.
Figure 3:
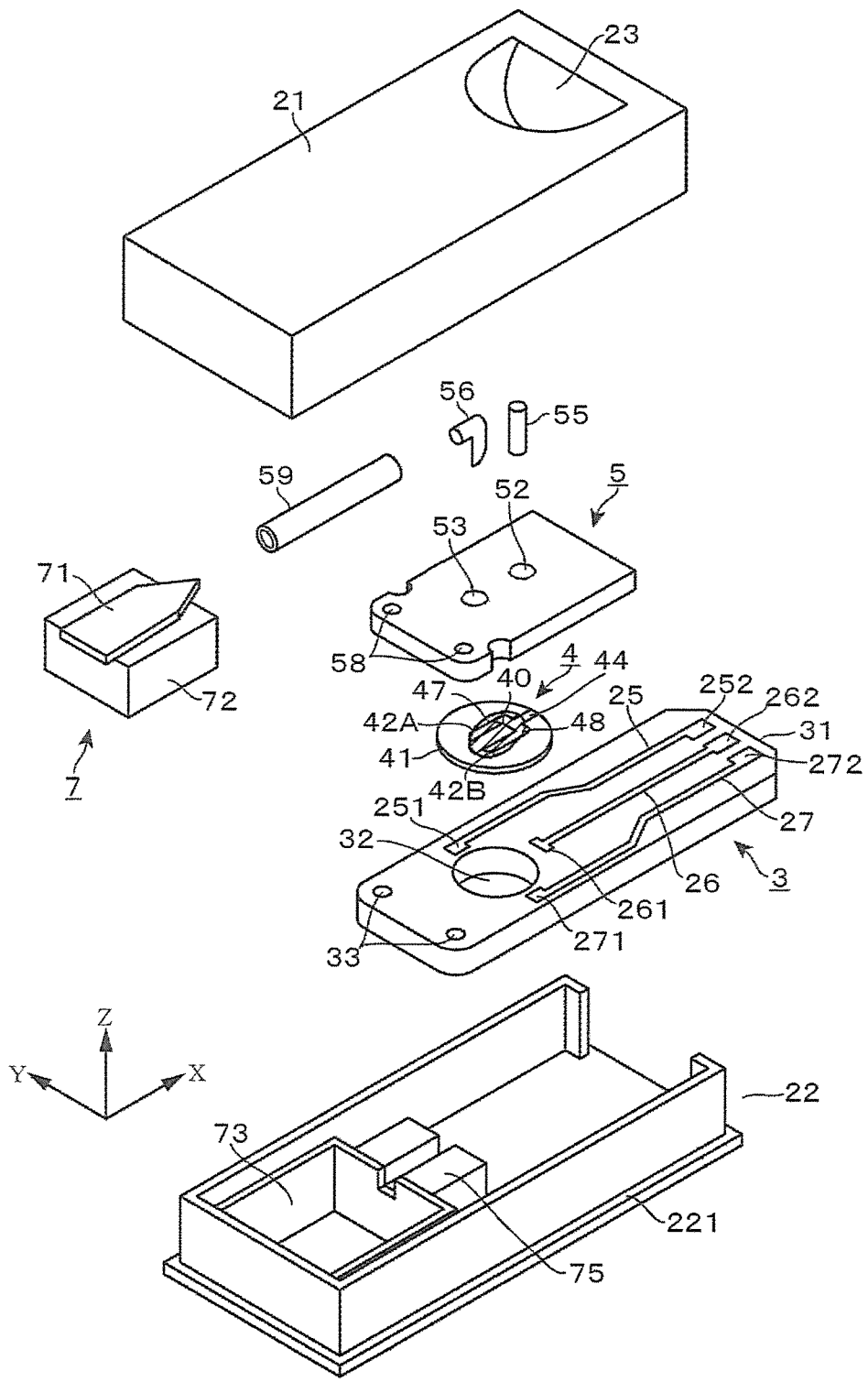
FIG. 3 is an exploded perspective view illustrating a top surface side of each portion of the sensing sensor.
Figure 4:
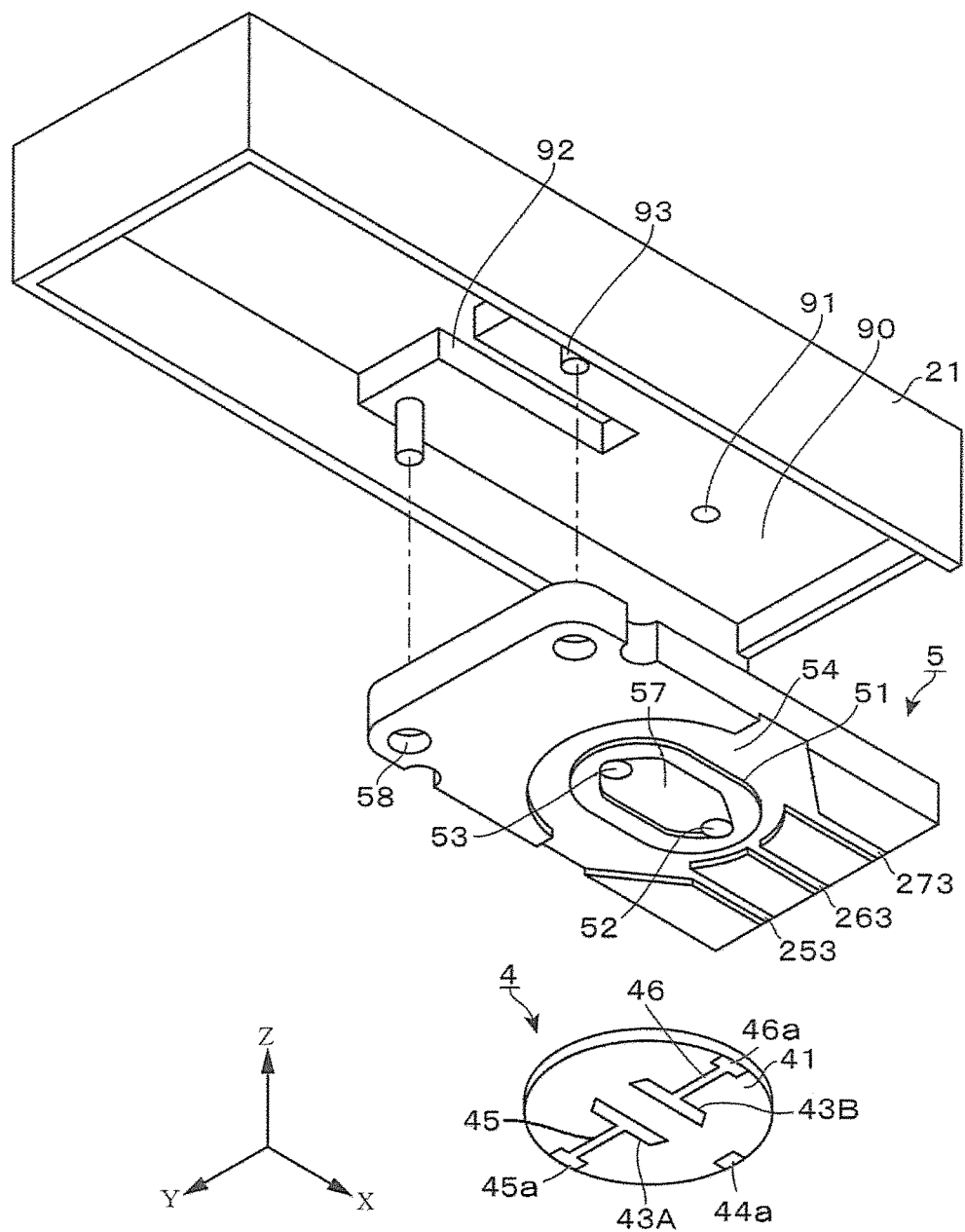
FIG. 4 is an exploded perspective view illustrating a lower surface side of a part of the sensing sensor.

Subsequently, the sensing sensor 2 will be described. FIG. 2 is a perspective view illustrating the sensing sensor 2, which is illustrated in FIG. 1, in a state where an upper-side cover body 21 is removed. FIG. 3 and FIG. 4 are perspective views illustrating a front side (top surface side) of each member of the sensing sensor 2 and a back surface (lower surface side) of some members, respectively. The sensing sensor 2 includes a container 20 constituted of the upper-side cover body 21 and a lower-side case 22 as illustrated in FIG. 2. A wiring board 3 with a shape extended in a longitudinal direction is arranged over the lower-side case 22 as illustrated in FIG. 3, and an insertion portion 31 that is inserted into the above-described insertion port 17 of the main body 12 is formed on one end side of the longitudinal direction in the wiring board 3. In the following description, the insertion portion 31 side of the sensing sensor 2 denotes the front, and the other end side denotes the rear.

At the position of the rear side of the wiring board 3, a through hole 32 is formed. The wiring board 3 is arranged such that the bottom surface of the lower-side case 22 covers the through hole 32, and the insertion portion 31 protrudes outside the lower-side case 22. The through hole 32 whose lower side is covered by the lower-side case 22 corresponds to a depressed portion. The wiring board 3 has a front surface on which three wirings 25 to 27 extending in the longitudinal direction are disposed. In the insertion portion 31, terminal portions 252, 262, and 272 are formed on one end side of the wirings 25, 26, and 27, respectively. In the outer edge of the through hole 32, terminal portions 251, 261 and 271 are formed on another end side of the wirings 25, 26, and 27, respectively. Further, in the further rear of the through hole 32 on the wiring board 3, two hole portions 33 for locating the horizontal position of the wiring board 3 are formed alongside in a width direction.

Next, a description will be given of a crystal resonator 4 by referring to FIG. 5A and FIG. 5B respectively illustrating its front surface side and back surface side. The crystal resonator 4 includes a circular-plate-shaped crystal element 41 formed of, for example, an AT-cut. The front surface side of the crystal resonator 4 includes a common electrode 42 made of, for example, gold (Au). The common electrode 42 has a front side to which two electrodes, a first and a second excitation electrodes 42A and 42B, disposed in parallel to one another are connected. The back surface side of the crystal resonator 4 includes a first and a second excitation electrodes 43A and 43B, which are made of, for example, Au, on positions respectively opposed to the first excitation electrode 42A and the second excitation electrode 42B. A region between the first excitation electrode 42A and the first excitation electrode 43A on the common electrode 42 of the crystal resonator 4 is a first vibrating region 61. A region between the second excitation electrode 42B and the second excitation electrode 43B is a second vibrating region 62. The first and the second vibrating regions 61 and 62 are disposed apart from one another and vibrate independently.

From the common electrode 42, an extraction electrode 44 extends toward a front side peripheral edge portion of the crystal element 41, and further extends on a side surface of the crystal element 41 to form a terminal portion 44a on a peripheral edge portion of the back surface of the crystal element 41. From the first and the second excitation electrodes 43A and 43B, extraction electrodes 45 and 46 are extracted toward a peripheral edge of the crystal element 41 to respectively form terminal portions 45a and 46a on the peripheral edge portion of the crystal element 41.

Figure 6:
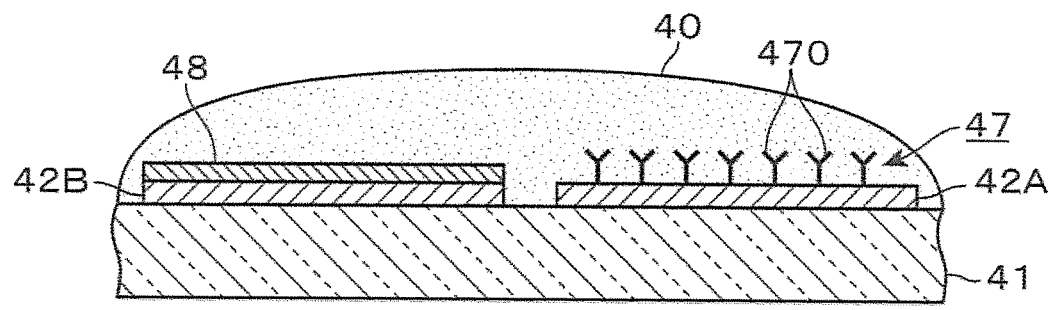
FIG. 6 is a sectional drawing illustrating a front surface of the crystal resonator on which a protective agent is applied.

With reference to FIG. 6, an adsorbing film 47 that is constituted of an antibody 470 selectively combining with a sensing object is arranged in the region, which serves as the first vibrating region 61, on the surface of the first excitation electrode 42A as one electrode of the common electrode 42. Further, on the common electrode 42, a blocking film 48 that inhibits adhesion of the sensing object to the surface is arranged in the region other than the region on which the adsorbing film 47 is disposed and on the extraction electrode 44.

Figure 5A:
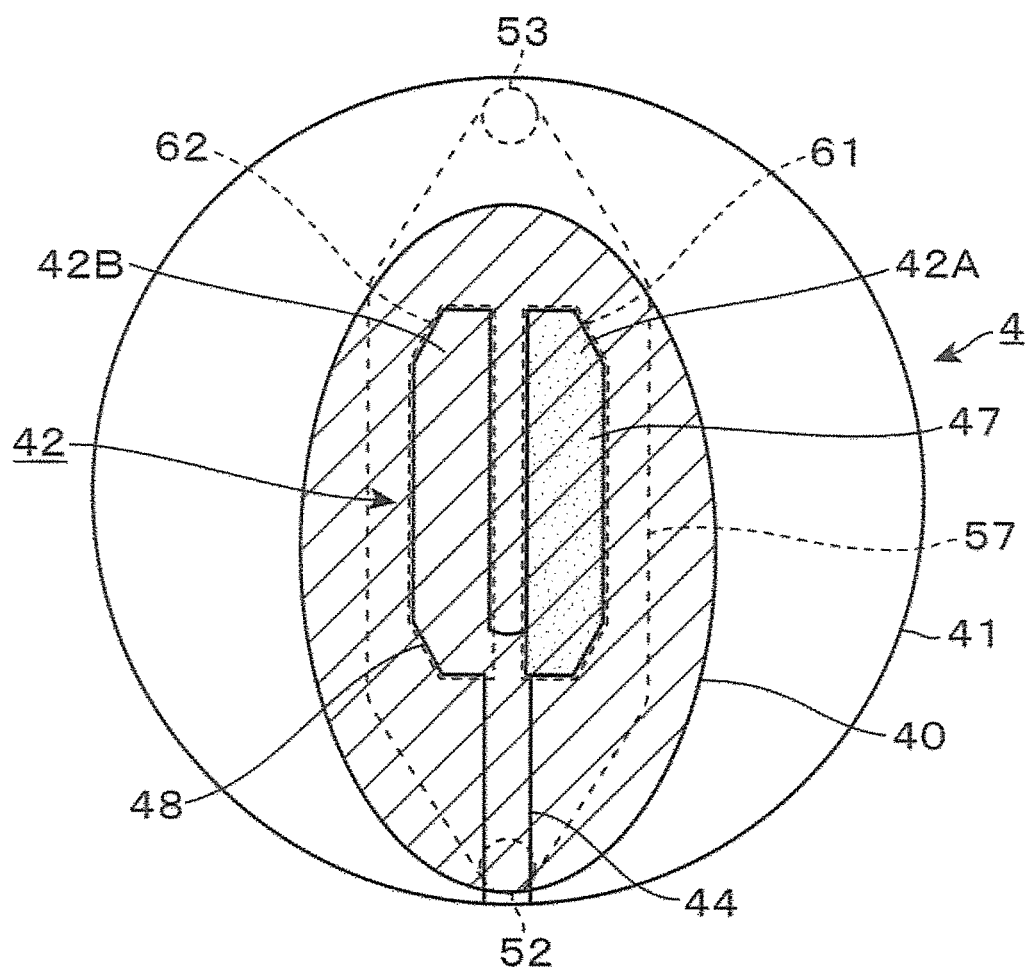
FIG. 5A is a plan view illustrating a front surface side of a crystal resonator.
Figure 5B:
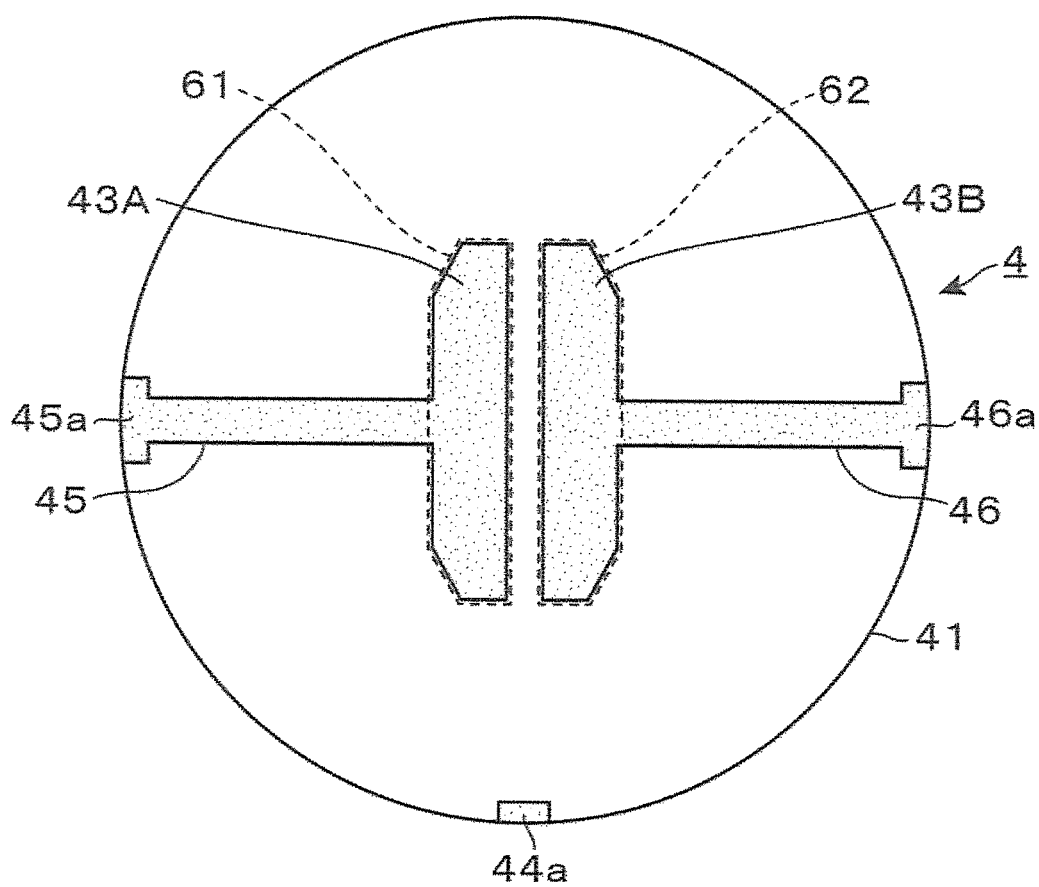
FIG. 5B is a plan view illustrating a back surface side of the crystal resonator.

After disposing the adsorbing film 47 and the blocking film 48, as illustrated in FIG. 5A and FIG. 6, a protective agent 40, which is constituted of a gel-like high viscosity material such as glycerin and sugar, is applied so as to cover the surface of the common electrode 42. This causes the entire surface of the common electrode 42 including the antibody 470, formed on the surface of the adsorbing film 47, and the blocking film 48 to be covered with the protective agent 40.

As illustrated in FIG. 3 and FIG. 4, the crystal resonator 4, over which the protective agent 40 is applied, is disposed such that the first and the second excitation electrodes 43A and 43B on the back surface side of the crystal resonator 4 face the through hole 32 of the wiring board 3. Then, the terminal portions 44a, 45a, and 46a are bonded to the respectively corresponding terminal portions 261, 251 and 271, disposed on the wiring board 3, by a conductive adhesive.

As illustrated in FIG. 3 and FIG. 4, a channel forming member 5 is arranged on the top surface side of the wiring board 3. The channel forming member 5 is constituted of a plate-shaped member made of, for example, polydimethylsiloxane (PDMS). On the position near to the rear of the channel forming member 5, hole portions 58 for positioning the channel forming member 5 are arranged on positions corresponding to the hole portions 33 arranged on the wiring board 3 such that the hole portions 58 pass through the channel forming member 5 in a thickness direction.

As illustrated in FIG. 4, an approximately circular-shaped depression 54 is provided so as to house the crystal resonator 4 on the inferior surface side of the channel forming member 5. On the inferior surface side of the channel forming member 5, grooves 253, 263, and 273 are formed to communicate with the depression 54, and to respectively house the wirings 25, 26, and 27 formed on the wiring board 3. On the depression 54, a surrounding portion 51 is arranged to partition and form a supply channel 57 for the sample solution with the front surface of the crystal resonator 4 when the channel forming member 5 is pressed to the wiring board 3 side. This surrounding portion 51 is constituted of an annular protrusion, the outer edge of which is formed in an oval shape, such that the longitudinal direction of the surrounding portion 51 aligns with the front-rear direction of the sensing sensor 2. The surrounding portion 51 is constituted so as to protrude from the depression 54 with a thickness of 300 µm, and the inside region of the surrounding portion 51 has a plane with height identical to the depression 54. The channel forming member 5 includes through holes 52 and 53 that have openings on the front end and the rear end of the supply channel 57, respectively, and pass through the channel forming member 5 in the thickness direction.

Figure 7:
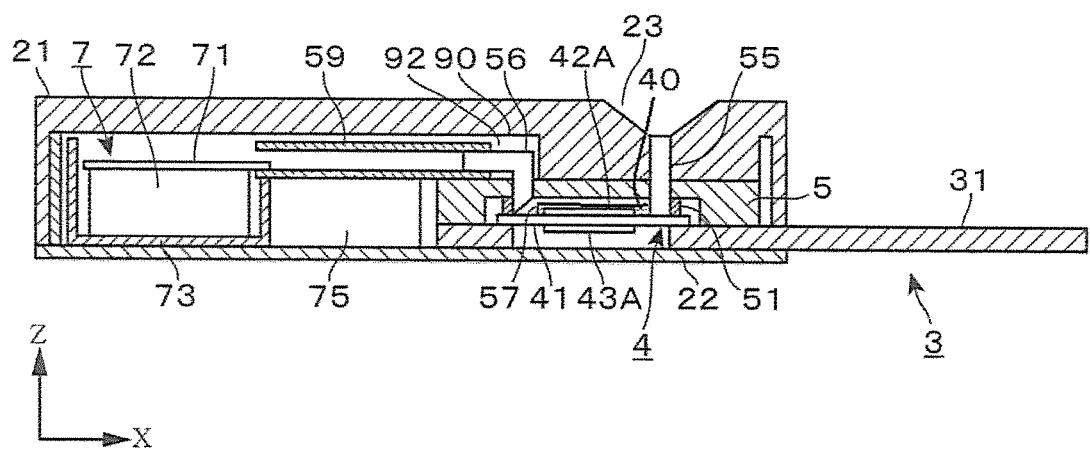
FIG. 7 is a vertical cross-sectional side view of the sensing sensor.

The channel forming member 5 includes the hole portions 58 arranged so as to align the hole portions 33 disposed on the wiring board 3. Then, the surrounding portion 51 is disposed on the top surface of the crystal resonator 4, and the inferior surface side of the supply channel 57 is covered with the crystal resonator 4. Then, the first and the second excitation electrodes 42A and 42B are aligned and housed on the center of the supply channel 57. Accordingly, as illustrated in FIG. 5A, the first and the second vibrating regions 61 and 62 are arranged so as to align on right and left with respect to a direction from the through hole 52 to the through hole 53. As illustrated in FIG. 7, the region surrounded by the surrounding portion 51 and the crystal resonator 4 has the bottom surface constituted of the crystal resonator 4 to form the supply channel 57 of 300 µm in depth with a ceiling surface and a bottom surface extending in parallel.

As illustrated in FIG. 3 and FIG. 7, the through holes 52 and 53 attachably/detachably include respectively an inlet-side capillary member 55 and an outlet-side capillary member 56 each constituted of a porous member. The inlet-side capillary member 55, for example, is a columnar member and constituted of a chemical fiber bundle, such as polyvinyl alcohol (PVA). The inlet-side capillary member 55 is disposed so as to cover the through hole 52. An upper end of the inlet-side capillary member 55 is disposed to be exposed to an injection port 23 formed on the upper-side cover body 21, which will be described later, and the lower end is disposed to enter into the supply channel 57. Similarly, the outlet-side capillary member 56 is constituted of a chemical fiber bundle, such as polyvinyl alcohol (PVA), and is formed in an L-shape by extending upward and subsequently bended to extend horizontally. The outlet-side capillary member 56 is disposed so as to cover the through hole 53, and a lower end of the outlet-side capillary member 56 is disposed to enter into the supply channel 57. Furthermore, the lower end of the outlet-side capillary member 56 is inclined to the rear side from the front side.

The other end side of the outlet-side capillary member 56 is inserted into one end side of an effluent channel 59 constituted of, for example, a hydrophilic glass tube. The other end side of the effluent channel 59 is connected to an effluent absorbing portion 7 constituted of, for example, a capillary sheet 71, which suctions liquid flown out from the effluent channel 59, and an absorbing member 72, which absorbs the liquid suctioned by the capillary sheet 71. The lower-side case 22 includes a case body 73 that houses the effluent absorbing portion 7 and prevents a liquid leakage from the absorbing member 72. Reference numeral 75 in the drawing is a supporting member that supports the effluent channel 59.

A description will be given of the upper-side cover body 21. As illustrated in FIG. 2 and FIG. 3, the lower-side case 22 houses the wiring board 3 except for the insertion portion 31, the crystal resonator 4, the channel forming member 5 to which the inlet-side capillary member 55 and the outlet-side capillary member 56 are connected, and the effluent channel 59 and the effluent absorbing portion 7. The upper-side cover body 21 is disposed to cover the surroundings of the lower-side case 22 from the upper side. On the top surface side of the upper-side cover body 21, the injection port 23 inclined in a cone shape is disposed. As illustrated in FIG. 4, the back surface side of the upper-side cover body 21 includes a pressing portion 90 for pressing the channel forming member 5 onto the wiring board 3. The pressing portion 90 is constituted to be in, for example, an approximate box shape and presses an entire top surface of the channel forming member 5 vertically downward with the lower surface of the pressing portion 90 when the upper-side cover body 21 is engaged and locked together with the lower-side case 22, so as to cause the surrounding portion 51 to be contacted with the crystal resonator 4. The pressing portion 90 includes a through hole 91 penetrating through the injection port 23 on the position corresponding to the through hole 52.

The pressing portion 90 includes a cutout 92 that ensures an installation area for the effluent channel 59 and the outlet-side capillary member 56 toward the rear side from the position corresponding to the through hole 53. Further, the pressing portion 90 includes fixing pillars 93 inserted in the hole portions 58 and 33, which are respectively disposed on the channel forming member 5 and the wiring board 3, and the fixing pillars 93 restrict a displacement of the channel forming member 5 and the wiring board 3.

Figure 8:
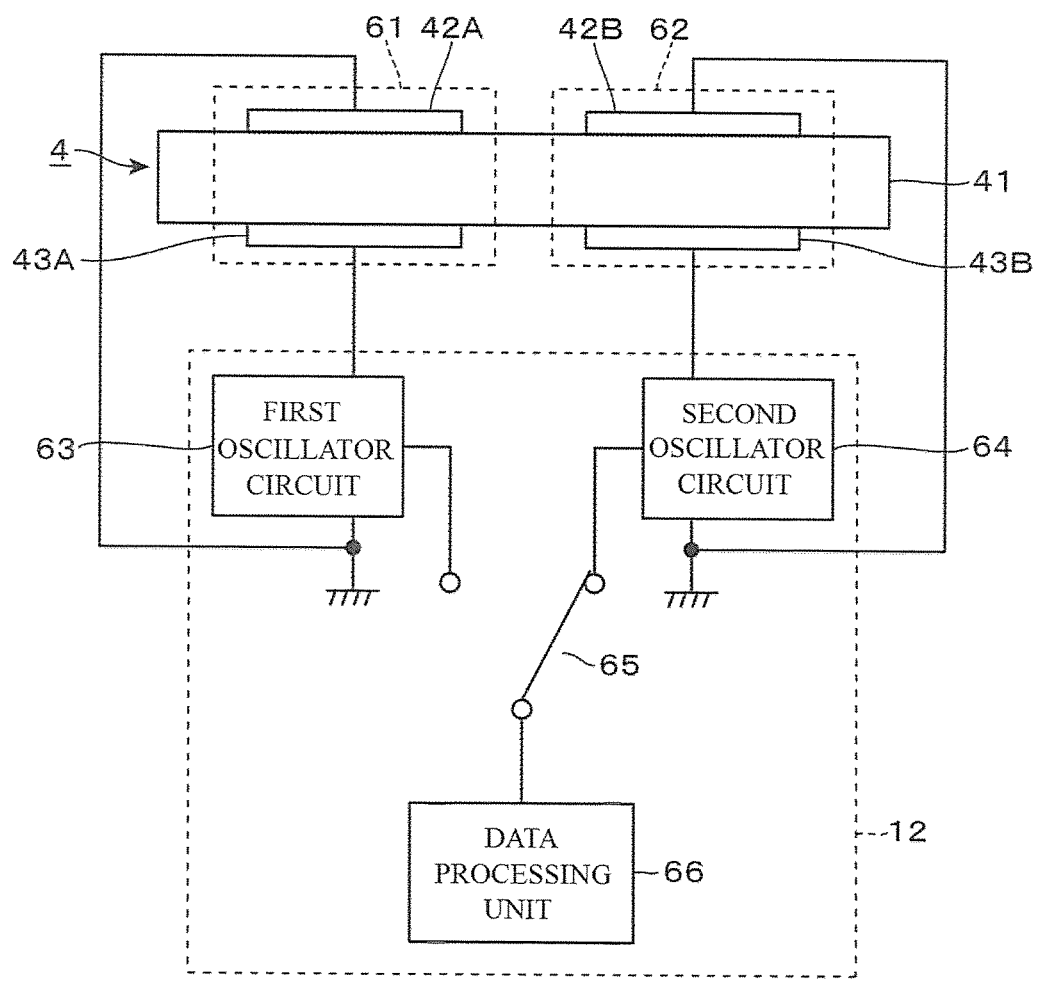
FIG. 8 is a schematic configuration view of the sensing device.

Subsequently, a description will be given of the whole configuration of the sensing device that uses the sensing sensor 2. Inserting the insertion portion 31 of the above-described sensing sensor 2 into the main body 12 electrically connects the terminal portions 252, 262, and 272 formed on the insertion portion 31 to connection terminal portions (not illustrated) formed on the main body 12 so as to correspond to the terminal portions 252, 262, and 272, thus constituting the sensing device schematically illustrated in FIG. 8. As illustrated in FIG. 8, the main body 12 includes a first oscillator circuit 63 and a second oscillator circuit 64 that are constituted of, for example, Colpitts circuits. The first oscillator circuit 63 is configured to oscillate the first vibrating region 61, which is the region between the first excitation electrode 42A and the first excitation electrode 43A on the crystal resonator 4, and the second oscillator circuit 64 is configured to oscillate the second vibrating region 62, which is the region between the second excitation electrode 42B and the second excitation electrode 43B. The first and the second excitation electrodes 42A and 42B on the top surface side of the crystal resonator 4 are connected so as to be a ground potential in the oscillation.

The output sides of the first and the second oscillator circuits 63 and 64 are connected to a switch 65, and a data processing unit 66 is arranged on the latter part of the switch 65. The data processing unit 66 digitizes a frequency signal as an input signal, and obtains time-series data of oscillation frequency "F1" output from the first oscillator circuit 63 and time-series data of oscillation frequency "F2" output from the second oscillator circuit 64.

The sensing device of this disclosure is configured to perform intermittent oscillation by alternately switching a channel 1 connecting the data processing unit 66 to the first oscillator circuit 63 and a channel 2 connecting the data processing unit 66 to the second oscillator circuit 64 by the switch 65, so as to ensure avoiding interference between the two vibrating regions 61 and 62 of the sensing sensor 2 to obtain the stable frequency signals. Subsequently, these frequency signals are, for example, time-shared and fed into the data processing unit 66. The data processing unit 66 calculates the frequency signals as, for example, digital values, thus performing arithmetic processing based on the time-shared data of the calculated digital values, so as to display the arithmetic operation result such as presence/absence of the antigen on the display 16.

Figure 9:
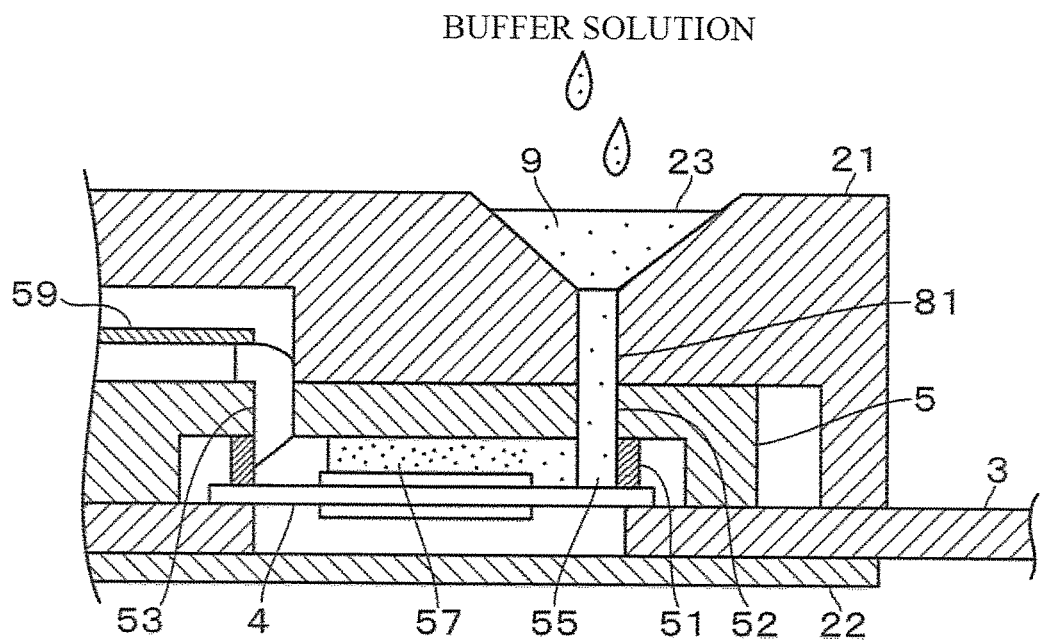
FIG. 9 is an explanatory drawing explaining an operation of the sensing sensor according to an embodiment of this disclosure.

Next, a description will be given of a method for determining presence/absence of the sensing object in the sample solution using the sensing sensor 2. First, the insertion portion 31 of a new sensing sensor 2 is inserted to the insertion port 17 of the main body 12 to connect the sensing sensor 2 to the main body 12. Subsequently, an injector (not illustrated) is used to inject a remover to the protective agent 40, for example, a phosphate buffer solution 9 into the injection port 23 as illustrated in FIG. 9. At this time, the phosphate buffer solution 9 is absorbed to the inlet-side capillary member 55 by a capillarity and flows inside the inlet-side capillary member 55, thus flowing into the supply channel 57 to be supplied to the front-side surface of the crystal resonator 4.

Since the surface of the crystal element 41 constituting the crystal resonator 4 is hydrophilic, the phosphate buffer solution 9 wets and spreads inside the supply channel 57. Then, subsequently to the phosphate buffer solution 9 spread in the supply channel 57, the phosphate buffer solution 9 in the inlet-side capillary member 55 is drawn out to the surface of the crystal element 41 by a surface tension, thus continuously flowing from the injection port 23 to the supply channel 57.

Figure 10:
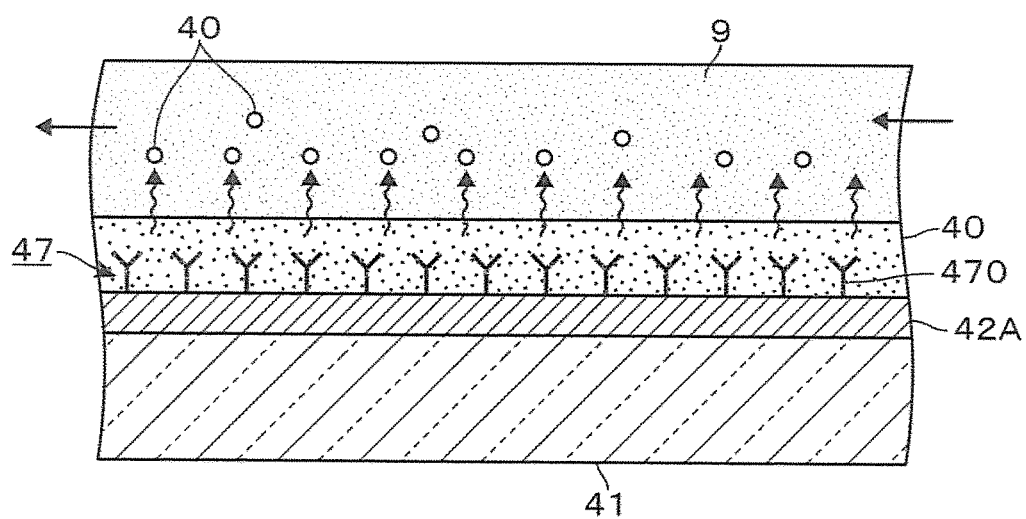
FIG. 10 is an explanatory drawing explaining a removal of the protective agent by a phosphate buffer.
Figure 11:
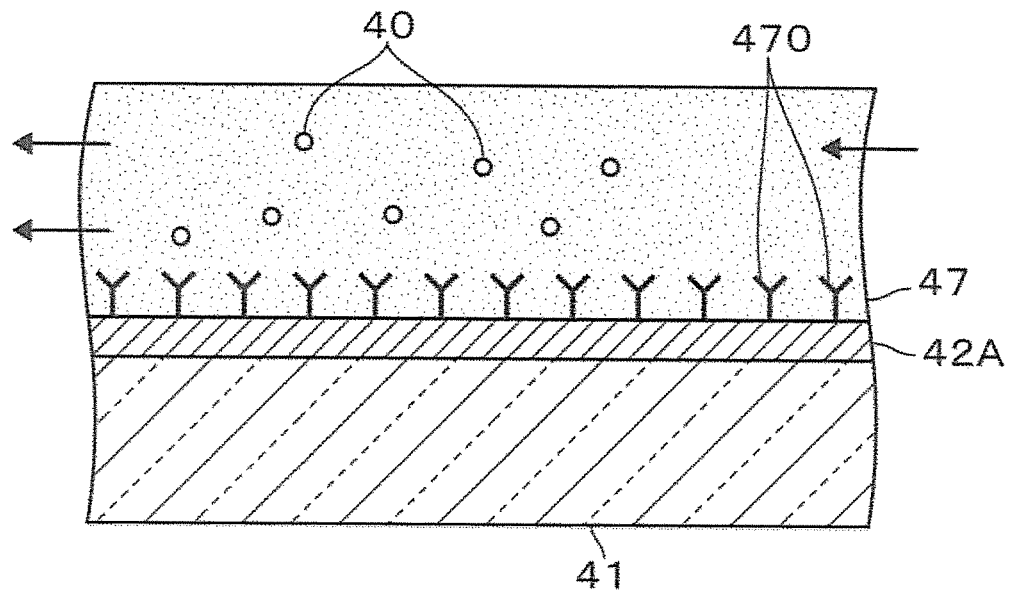
FIG. 11 is an explanatory drawing explaining the removal of the protective agent by the phosphate buffer.

When the phosphate buffer solution 9 fills the supply channel 57, as illustrated in FIG. 10, the protective agent 40 contacts the phosphate buffer solution 9. Since the protective agent 40 is constituted of such as glycerin and sugar, the protective agent 40 is gradually dissolved in the phosphate buffer solution 9. As illustrated in FIG. 11, this gradually removes the protective agent 40 disposed so as to cover the surface of the common electrode 42, thus causing the adsorbing film 47 on the surface of the first excitation electrode 42A to be exposed. On the surface of the second excitation electrode 42B, the blocking film 48 is exposed.

Figure 12:
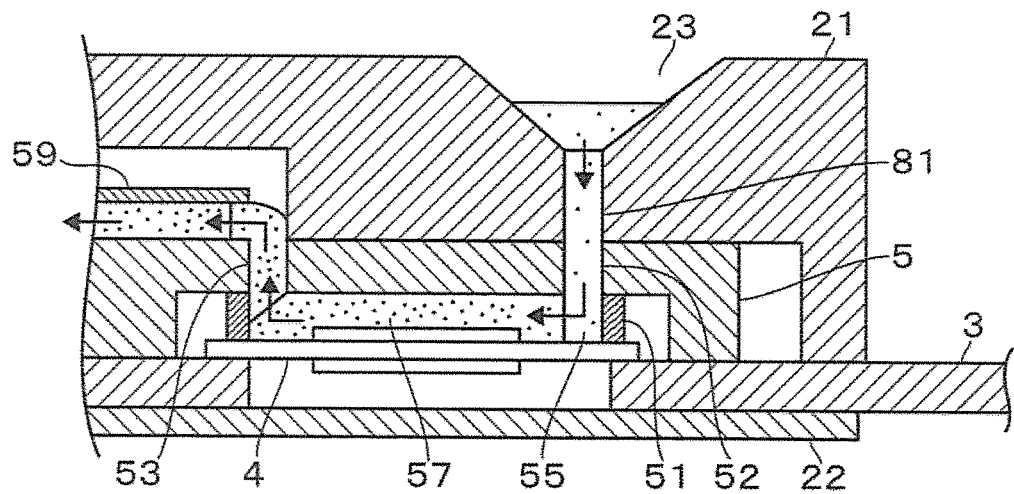
FIG. 12 is an explanatory drawing explaining a flow of a liquid supplied to the sensing sensor.

Then, as illustrated in FIG. 12, when the phosphate buffer solution 9 flowing on the front surface of the crystal resonator 4 reaches the outlet-side capillary member 56, the phosphate buffer solution 9 is absorbed in the outlet-side capillary member 56 by the capillarity and flows inside the outlet-side capillary member 56 to exude to the effluent channel 59. Here, due to workings of the principle of the siphon in addition to the capillarity, the phosphate buffer solution 9 that has been continuously supplied to the injection port 23 passes through the front surface of the crystal resonator 4 to be discharged to the effluent channel 59. Then, since the protective agent 40 that has covered the common electrode 42 is dissolved in the phosphate buffer solution 9, the protective agent 40 is discharged to the effluent channel 59 with the phosphate buffer solution 9.

The phosphate buffer solution 9 inside the effluent channel 59 flows inside the effluent channel 59 to the downstream and reaches the capillary sheet 71. When the phosphate buffer solution 9 inside the effluent channel 59 reaches the capillary sheet 71, the phosphate buffer solution 9 is absorbed in the capillary sheet 71 side at a speed higher than a moving speed of the phosphate buffer solution 9 flowing through the effluent channel 59. Then, the phosphate buffer solution 9 is spread to flow on the capillary sheet 71 by the capillarity. At this time, a state where the phosphate buffer solution 9 is interrupted is formed in the effluent channel 59.

Thus, when the phosphate buffer solution 9 is separated through the effluent channel 59, the phosphate buffer solution 9 on the capillary sheet 71 side is absorbed into and retained in the absorbing member 72 that contacts with the capillary sheet 71. Meanwhile, since the phosphate buffer solution 9 remaining in the injection port 23 attempts to flow toward the effluent channel 59 by the capillarity and the principle of siphon, this flow of the phosphate buffer solution 9 causes the phosphate buffer solution 9 remaining in the effluent channel 59 to move to the downstream side, so as to contact the capillary sheet 71 again. Thus repeating the separation of the phosphate buffer solution 9 and the flow of the phosphate buffer solution 9 in the effluent channel 59 causes the phosphate buffer solution 9 in the supply channel 57 to flow into the effluent channel 59. Thus, all the phosphate buffer solution 9 in which the protective agent 40 is dissolved is discharged to the effluent channel 59. Then, when all the phosphate buffer solution 9 in the injection port 23 flows out, a force that drifts the phosphate buffer solution 9 to the downstream is decreased, and the phosphate buffer solution 9 stops in a state of being separated in the effluent channel 59. Accordingly, a state where the supply channel 57 is filled with the subsequent phosphate buffer solution 9, that is, the phosphate buffer solution 9 without the protective agent 40 is generated. As described above, since the protective agent 40 applied over the front surface of the crystal resonator 4 is removed, the adsorbing film 47 and the blocking film 48 are also exposed to come into a state of contacting with the phosphate buffer solution 9.

Subsequently, the sample solution is supplied to the injection port 23. This increases a pressure applied to the phosphate buffer solution 9 absorbed in the inlet-side capillary member 55 and causes the phosphate buffer solution 9 to flow toward the downstream inside the effluent channel 59 again, and thus the sample solution injected into the injection port 23 is absorbed into the inlet-side capillary member 55. The sample solution absorbed by the inlet-side capillary member 55 flows into the supply channel 57 from the inlet-side capillary member 55 similarly to the phosphate buffer solution 9. This drifts the phosphate buffer solution 9, which fills the supply channel 57, to the downstream to be absorbed by the outlet-side capillary member 56, so as to be discharged from the supply channel 57. Consequently, the phosphate buffer solution 9 is replaced with the sample solution inside the supply channel 57.

Since the first and second excitation electrodes 42A and 42B are symmetrically formed when viewed from the inlet side to the outlet side of the supply channel 57, these first and second excitation electrodes 42A and 42B equally receive a pressure variation by replacement of the liquid inside the supply channel 57. Thus, the oscillation frequencies of the first vibrating region 61 and the second vibrating region 62 by the pressure variation vary all together with one another. When the sample solution includes the sensing object, the adsorbing film 47 on the first excitation electrode 42A adsorbs the sensing object. On the other hand, the sensing object is not adsorbed on the second excitation electrode 42B because the blocking film 48 is disposed. This decreases the frequency of the first vibrating region 61 corresponding to the amount of adsorption of the sensing object to the adsorbing film 47. Accordingly, for example, when the data processing unit 66 obtains an amount of frequency variation F1-F2 as a difference value between an oscillation frequency F1, which is output from the first oscillator circuit 63, and an oscillation frequency F2, which is output from the second oscillator circuit 64, the amount of frequency variation F1-F2 varies corresponding to the amount of adsorption of the sensing object to the adsorbing film 47. Thus the sensing sensor 2 ensures determining the presence/absence of the sensing object based on the variation of the amount of frequency variation F1-F2.

Here, the sensing sensor 2 is stored in a new condition where the surface of the common electrode 42 is covered with the protective agent 40. The antibody 470 constituting the adsorbing film 47 is sometimes denatured to decrease the adsorption capacity due to, for example, drying and materials contained in the atmosphere. However, the protective agent 40 has a high moisturizing ability because the protective agent 40 is gel-like with the high viscosity such as glycerin and sugar, so as to prevent the adsorbing film 47 from drying, thus inhibiting the adsorbing film 47 from contacting with the atmosphere to suppress the denaturation of the biomolecules. Since sugar and glycerin can maintain the structure of the biomolecules, the structure of the biomolecules of such as the antibody 470 can be protected while it is maintained when the adsorbing film 47 is covered with the protective agent 40.

Furthermore, a state where the protective agent 40 is attached on the front surface of the crystal resonator 4 prevents the oscillation of the crystal resonator 4. Therefore, when the sensing sensor 2 is connected to the main body 12 for the measurement, it is necessary to remove the protective agent 40 from the front surface of the crystal resonator 4. In the above-described embodiment, supplying the phosphate buffer solution 9 to the injection port 23 of the sensing sensor 2 causes the phosphate buffer solution 9 to flow through the supply channel 57, through which the sample solution flows, via the inlet-side capillary member 55, so as to ensure removing the protective agent 40. This removes the protective agent 40 and causes the adsorbing film 47 to be exposed with a simple method without performing processes such as decomposition, cleaning, drying, and assembling of the sensing sensor 2, so as to ensure the measurement of the sample solution.

In the above-described embodiment, in the sensing sensor 2 that causes the sensing object to be adsorbed on the adsorbing film 47, which is formed on the surface of the first excitation electrode 42, to sense the sensing object, the protective agent 40 constituted of the high viscosity material is applied so as to cover the surface of the adsorbing film 47 in the sensing sensor 2. This ensures the reduction of the drying and the deterioration of the adsorbing film 47 when the sensing sensor 2 is stored. Then, when the sensing sensor 2 is used, flowing the phosphate buffer solution 9 through the supply channel 57, which causes the sample solution to flow on the front surface of the crystal resonator 4, disposed on the sensing sensor 2 removes the protective agent 40. This exposes the adsorbing film 47 with a simple operation, so as to ensure the measurement of the sensing object.

The phosphate buffer solution 9 may be injected into the sensing sensor 2 before the sensing sensor 2 is connected to the main body 12 of the sensing device. As illustrated in FIG. 9 to FIG. 12, the sample solution injected into the injection port 23 flows through the supply channel 57 by the capillarity and the principle of siphon. This ensures the phosphate buffer solution 9 to flow on the front surface of the crystal resonator 4 even before the sensing sensor 2 is connected to the main body 12 of the sensing device, so as to wash away the protective agent 40.

The adsorbing film 47 may be the adsorbing film 47 constituted of such as protein and nucleic acid. The biomolecules such as protein and nucleic acid is easily inactivated due to the contact the atmosphere and the drying. Therefore, covering the adsorbing film 47 with the protective agent 40 suppresses the inactivation of the biomolecules, thus reducing the decrease of the adsorption capacity of the adsorbing film 47. Further, employing glycerin and sugar for the protective agent 40 protects the structure of the biomolecules while it is maintained, thus providing a similar effect.

While it is only necessary for the remover for removing the protective agent 40 to be a liquid that can wash away the protective agent 40, for example, the phosphate buffer solution 9 indicated in the embodiment, a normal saline, and other buffer solutions can be employed. Employing an isotonic solution that does not inhibit the activation of the biomolecules reduces a possibility to cause the biomolecules to be inactivated due to the component of the liquid when the adsorbing film 47 is exposed, thus it is preferable.

Figure 13:
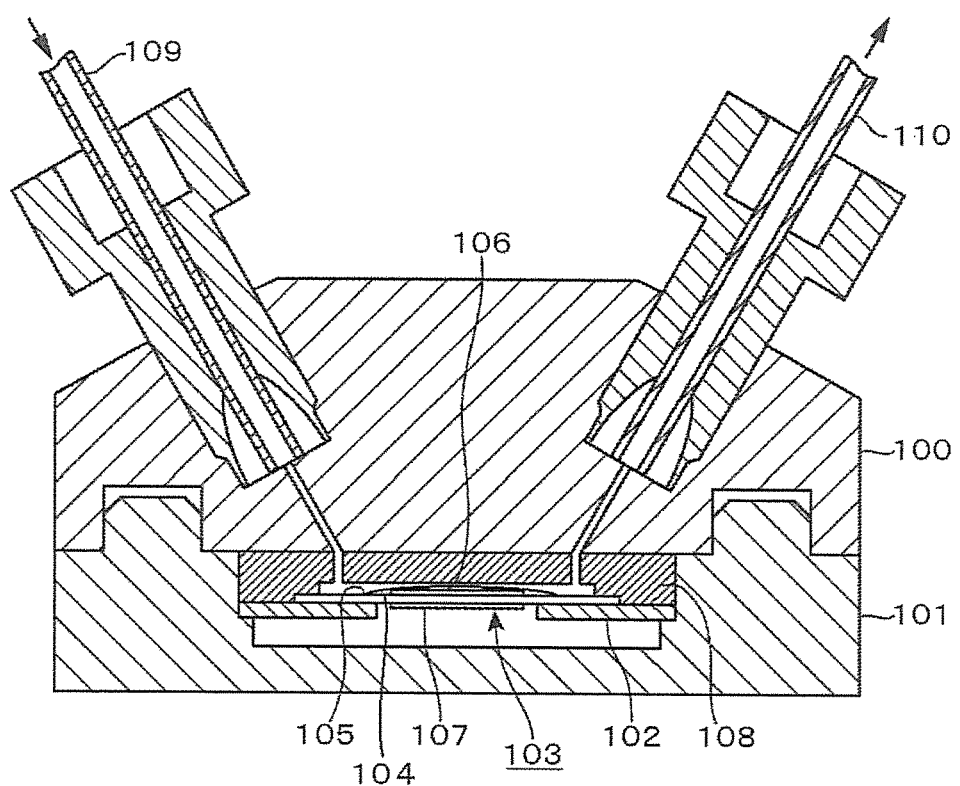
FIG. 13 is a vertical cross-sectional view illustrating another example of the embodiment of this disclosure.

This disclosure is not limited to the sensing sensor 2 that uses the capillarity to supply the sample solution to the crystal resonator 4, and a sensing device that uses a flow-type sensing sensor that flows a sample solution may be employed. FIG. 13 illustrates such sensing device. In FIG. 13, reference numeral 100 denotes an upper member, reference numeral 101 denotes a lower member, reference numeral 102 denotes a wiring board, reference numeral 103 denotes a crystal resonator, reference numeral 105 denotes a crystal element, reference numerals 106 and 107 denote electrodes, reference numeral 108 denotes a pressing member, reference numeral 109 denotes a liquid supply port, and reference numeral 110 denotes a liquid discharge port. The upper member 100 is constituted to be separable with respect to the lower member 101, and thus the crystal resonator 103 is replaceable. On the surface of the electrode 106 of the crystal resonator 103, similarly to the crystal resonator illustrated in FIG. 5A and FIG. 5B, an adsorbing film (not illustrated) constituted of the biomolecules is formed, and the protective agent 104 is applied so as to cover the electrode 106 on the flow passage, through which the sample solution flows, side.

The flow-type measuring unit causes the sample solution to flow from the liquid supply port 109 to the liquid discharge port 110 side via the space on the front surface side of the crystal resonator 103, and measures the oscillation frequency of the crystal resonator 103 while a reference solution or the sample solution are flown. In the case where such sensing device is used, flowing the phosphate buffer solution 9 on the front surface of the crystal resonator 103 after the sensing sensor is connected to the main body 12 removes the protective agent 104 to cause the adsorbing film to be exposed. Even in this case, the flow passage for the sample solution to flow can be used to flow the phosphate buffer solution 9, so as to ensure removing the protective agent 40 with the simple method to cause the adsorbing film to be exposed.

Working Example

The following test was performed for verifying the effect of the embodiment of this disclosure. The working example employed the example that used the sensing sensor 2 indicated in the above-described embodiment. Further, a comparative example employed an example configured similarly to the working example except that the protective agent 40 was not applied. After an accelerated test where the samples according to the working example and the comparative example are packed in an aluminum bag in a vacuum state and stored at 40° C. for three weeks is performed, the samples are connected to the main body 12 indicated in the embodiment to measure CRP (100 ng/ml), so as to measure the oscillation frequency to examine the variation of the amount of frequency variation F1-F2 according to the measuring method indicated in the embodiment. Further, the samples according to the working example and the comparative example are connected to the main body 12 indicated in the embodiment before the accelerated test to measure CRP (100 ng/ml), so as to examine the amount of frequency variation (F1-F2).

Under a high temperature environment storage, the crystal resonator 4 causes a frequency variation referred to as an aging deterioration. The aging deterioration is what is called a thermal activation process where the higher the storage temperature becomes, the more the frequency variation amount increases. The amount of the frequency variation after the storage at 40° C. for 21 days corresponds to the amount of the frequency variation in a case where two months passed at a room temperature (25° C.).

Figure 14:
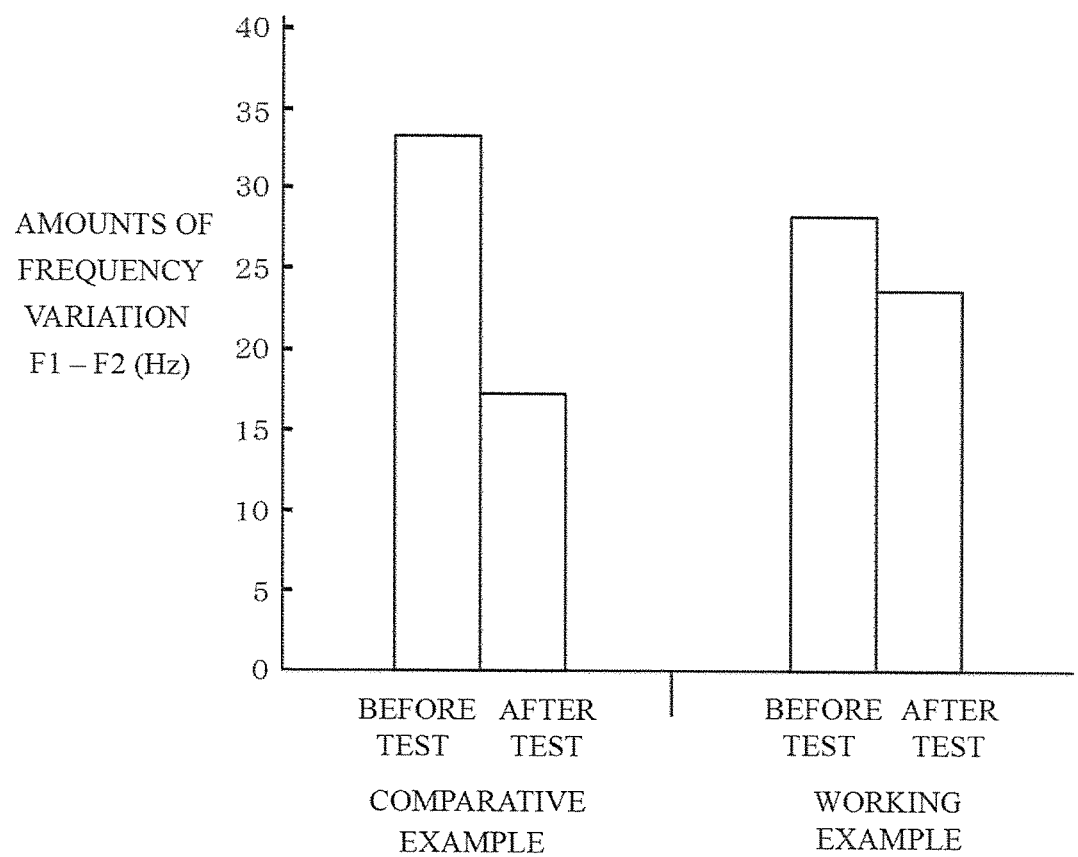
FIG. 14 is a characteristic diagram illustrating a frequency variation amount before and after a test in a working example and a comparative example.

FIG. 14 indicates the result and is a characteristic diagram that indicates the amounts of frequency variation (F1-F2) of the sensing sensors according to the comparative example and the working example measured before and after the accelerated test (indicating the result of before the test and after the test of each sensing sensor).

According to the result, in the comparative example, the amount of frequency variation (F1-F2) before the accelerated test is 32.5 Hz, and the amount of frequency variation (F1-F2) after the accelerated test is 17.5 Hz. The accelerated test decreases the amount of frequency variation (F1-F2) to 53%.

On the other hand, in the working example, the amount of frequency variation (F1-F2) before the accelerated test is 29.2 Hz, and the amount of frequency variation (F1-F2) after the accelerated test is 24 Hz. The accelerated test decreases the amount of frequency variation (F1-F2) to 82%.

Accordingly, this disclosure ensures reducing the decrease of the amount of frequency variation (F1-F2) when a new sensing sensor 2 is stored.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sensing sensor comprising:
   a wiring board that includes a connection terminal and a depressed portion, wherein the connection terminal is formed on one side of the wiring board for connection to a measuring device for measuring an oscillation frequency, the depressed portion is formed on one surface side of the wiring board;
   a piezoelectric resonator that includes a piezoelectric piece, an excitation electrode and an extraction electrode on the piezoelectric piece, the piezoelectric resonator being secured to the wiring board such that the piezoelectric resonator covers the depressed portion and a vibrating region is opposed to the depressed portion, the excitation electrode being electrically connected to the connection terminal, the piezoelectric resonator having one surface side on which an adsorbing film constituted of biomolecules for adsorbing a sensing object in a sample solution is formed, and a blocking film that inhibits adhesion of the sensing object to a surface is arranged in a region other than a region on which the adsorbing film is formed and on the extraction electrode;
   a protective agent having a high viscosity, disposed to cover a surface of the adsorbing film for suppressing an inactivation of the biomolecules;
   a channel forming member disposed to cover a region of the one surface side of the wiring board including the piezoelectric resonator, the channel forming member including an injection port of the sample solution; and
   a flow passage that is disposed between the wiring board and the channel forming member and allowing the sample solution supplied to the injection port to flow from one end side to another end side on the one surface side of the piezoelectric resonator.

2. The sensing sensor according to claim 1, comprising:

an effluent channel disposed on a downstream side of the flow passage, the effluent channel discharging the sample solution in the flow passage by a capillarity action;

a capillary member disposed on a downstream side of the effluent channel to contact the sample solution flowing through the effluent channel and allow the sample solution to flow by the capillarity action; and an absorbing member disposed on a downstream side of the capillary member to absorb the sample solution flowing through the capillary member.

3. The sensing sensor according to claim 2, wherein the protective agent is constituted of at least one of glycerin and sugar.

4. The sensing sensor according to claim 1, wherein the protective agent is constituted of at least one of glycerin and sugar.

* * * * *